(12) United States Patent
Lin et al.

(10) Patent No.: US 10,088,496 B2
(45) Date of Patent: Oct. 2, 2018

(54) CALIBRATION METHOD AND SPORTS EQUIPMENT

(71) Applicant: Wistron Corporation, New Taipei (TW)

(72) Inventors: Zhao-Yuan Lin, New Taipei (TW); Ming-Chih Ko, New Taipei (TW)

(73) Assignee: Wistron Corporation, New Taipei (TW)

( * ) Notice: Subject to any disclaimer, the term of this patent is extended or adjusted under 35 U.S.C. 154(b) by 237 days.

(21) Appl. No.: 14/961,833

(22) Filed: Dec. 7, 2015

(65) Prior Publication Data
US 2017/0056723 A1    Mar. 2, 2017

(30) Foreign Application Priority Data
Aug. 27, 2015 (TW) ............................. 104128079 A

(51) Int. Cl.
| | | |
|---|---|---|
| *G01P 21/00* | (2006.01) | |
| *G01C 25/00* | (2006.01) | |
| *A63B 60/46* | (2015.01) | |
| *G01P 15/18* | (2013.01) | |
| *A61B 5/11* | (2006.01) | |

(Continued)

(52) U.S. Cl.
CPC ............... *G01P 21/00* (2013.01); *A61B 5/11* (2013.01); *A63B 60/46* (2015.10); *G01P 15/18* (2013.01); *G06K 9/00342* (2013.01); *G09B 19/0038* (2013.01); *A63B 53/00* (2013.01); *G01C 25/00* (2013.01); *G01C 25/005* (2013.01)

(58) Field of Classification Search
CPC ....... G01P 21/00; G01C 25/00; G01C 25/005; A63B 60/46
See application file for complete search history.

(56) References Cited

U.S. PATENT DOCUMENTS

| | | | |
|---|---|---|---|
| 6,224,493 B1 | 5/2001 | Lee | |
| 7,771,263 B2 * | 8/2010 | Telford | ............. A63B 24/0003 463/3 |

(Continued)

FOREIGN PATENT DOCUMENTS

CN        102023700 B      6/2012

OTHER PUBLICATIONS

Office action dated Aug. 10, 2016 for TW application No. 104128079, filed: Aug. 27, 2015, p. 1 line 7~14, pp. 2~4 and p. 5 line 1~25.

*Primary Examiner* — Lisa Caputo
*Assistant Examiner* — Herbert K Roberts
(74) *Attorney, Agent, or Firm* — Winston Hsu

(57) ABSTRACT

A calibration method for a first accelerometer is disclosed. The first accelerometer is installed together with a second accelerometer in a device. The calibration method includes the second accelerometer measuring a first set of X, Y, Z accelerations in a Cartesian coordinate system, the first accelerometer measuring a second set of X, Y, Z accelerations in the Cartesian coordinate system, indicating to rotate the device, the second accelerometer measuring a third set of X, Y, Z accelerations in the Cartesian coordinate system, the first accelerometer measuring a fourth set of X, Y, Z accelerations in the Cartesian coordinate system, and calibrating X, Y, Z acceleration values measured by the first accelerometer based on the first, second, third and fourth sets of X, Y, Z accelerations.

3 Claims, 5 Drawing Sheets

(51) Int. Cl.
*G06K 9/00* (2006.01)
*G09B 19/00* (2006.01)
*A63B 53/00* (2015.01)

(56) References Cited

U.S. PATENT DOCUMENTS

| | | | |
|---|---|---|---|
| 8,459,094 B2 * | 6/2013 | Yanni | G01P 21/00 |
| | | | 73/1.38 |
| 8,762,091 B1 * | 6/2014 | Foxlin | G01P 15/00 |
| | | | 702/87 |
| 2009/0217733 A1 | 9/2009 | Stachow | |
| 2014/0364770 A1 * | 12/2014 | Slonneger | A61B 5/4812 |
| | | | 600/595 |

* cited by examiner

… (1)

CALIBRATION METHOD AND SPORTS EQUIPMENT

BACKGROUND OF THE INVENTION

1. Field of the Invention

The present invention relates to a calibration method and sports equipment, and more particularly, to a calibration method and sports equipment calibrating a high gravity accelerometer in reference to a low gravity accelerometer.

2. Description of the Prior Art

With advances in Microelectromechanical systems (MEMS), sports equipments are embedded with various kinds of accelerometers or G-sensors to record usage data for athletes. The recorded data can be utilized for analyzing athletic skills. For example, baseball bats and golf clubs are embedded with the accelerometers to record data of bat (or club) swing traces. These data are analyzed by computers to simulate the swing traces on display monitors. As a result, the athletes can repeatedly examine their own swing traces to improve athletic skills.

Please refer to FIG. 1, which is a schematic diagram of a simulated golf swing trace 10 of the prior art. In order to simulate the swing trace 10, acceleration data recorded by accelerometers embedded in a head 110 of a golf club 100 are required. Note that, the accelerations of the head 110 during swing and collision are significantly different due to Golf characteristics. Therefore, both low gravity and high gravity accelerometers are installed in the head 110. The low gravity and high gravity accelerometers are classified based on their top measurement limits. For example, the top measurement limits of the low gravity accelerometers are two, four or eight times gravity. On the other hand, the top measurement limits of the high gravity accelerometers can reach 100, 200 or 400 times gravity.

Generally, a typical measurement error of the accelerometers 1%, which means that a measurement error of an 8 G accelerometer is 0.08 G (G=9.8 m/s$^2$), which is tolerable inmost applications. However, a measurement error of a 400 G accelerometer can reach 4 G, which would result in a serious simulation error for swing trace reconstruction.

Therefore, the industry focuses on reducing the measurement error by calibrating the high gravity accelerometers.

SUMMARY OF THE INVENTION

It is therefore an objective of the present invention to provide a calibration method and sports equipment capable of reducing measurement errors for accelerometers.

An embodiment of the invention discloses a calibration method for calibrating a first accelerometer, the first accelerometer installed together with a second accelerometer in a device, the calibration method comprising the second accelerometer measuring a first set of X, Y, Z accelerations in a Cartesian coordinate system; the first accelerometer measuring a second set of X, Y, Z accelerations in the Cartesian coordinate system; indicating to rotate the device; the second accelerometer measuring a third set of X, Y, Z accelerations in the Cartesian coordinate system; the first accelerometer measuring a fourth set of X, Y, Z accelerations in the Cartesian coordinate system; and calibrating X, Y, Z acceleration values measured by the first accelerometer according to the first, second, third and fourth sets of X, Y, Z accelerations.

An embodiment of the invention further discloses a sports equipment, comprising a shaft; a head, installed at one end of the shaft, comprising a first accelerometer; a second accelerometer; a processing means; a storage unit, for storing a program code, wherein the program code is utilized for instructing the processing means to perform a calibration process; and an interface unit, for outputting data; and an indicative button, for activating the calibration process, the calibration process comprising instructing the second accelerometer to measure a first set of X, Y, Z accelerations in a Cartesian coordinate system; instructing the first accelerometer to measure a second set of X, Y, Z accelerations in the Cartesian coordinate system; driving the indicative button to display a signal, wherein the signal is utilized for indicating to rotate the head; instructing the second accelerometer to measure a third set of X, Y, Z accelerations in the Cartesian coordinate system; and instructing the first accelerometer to measure a fourth set of X, Y, Z accelerations in the Cartesian coordinate system.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
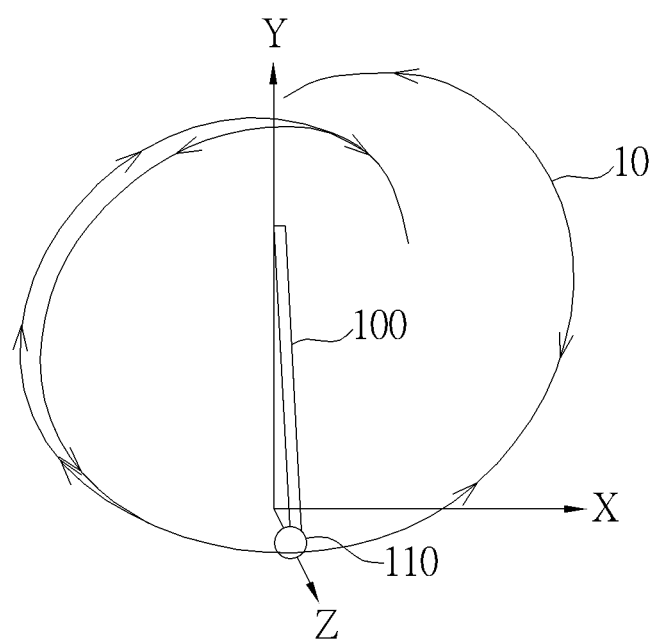
FIG. 1 is a schematic diagram of a simulated golf swing trace of the prior art.
Figure 2:
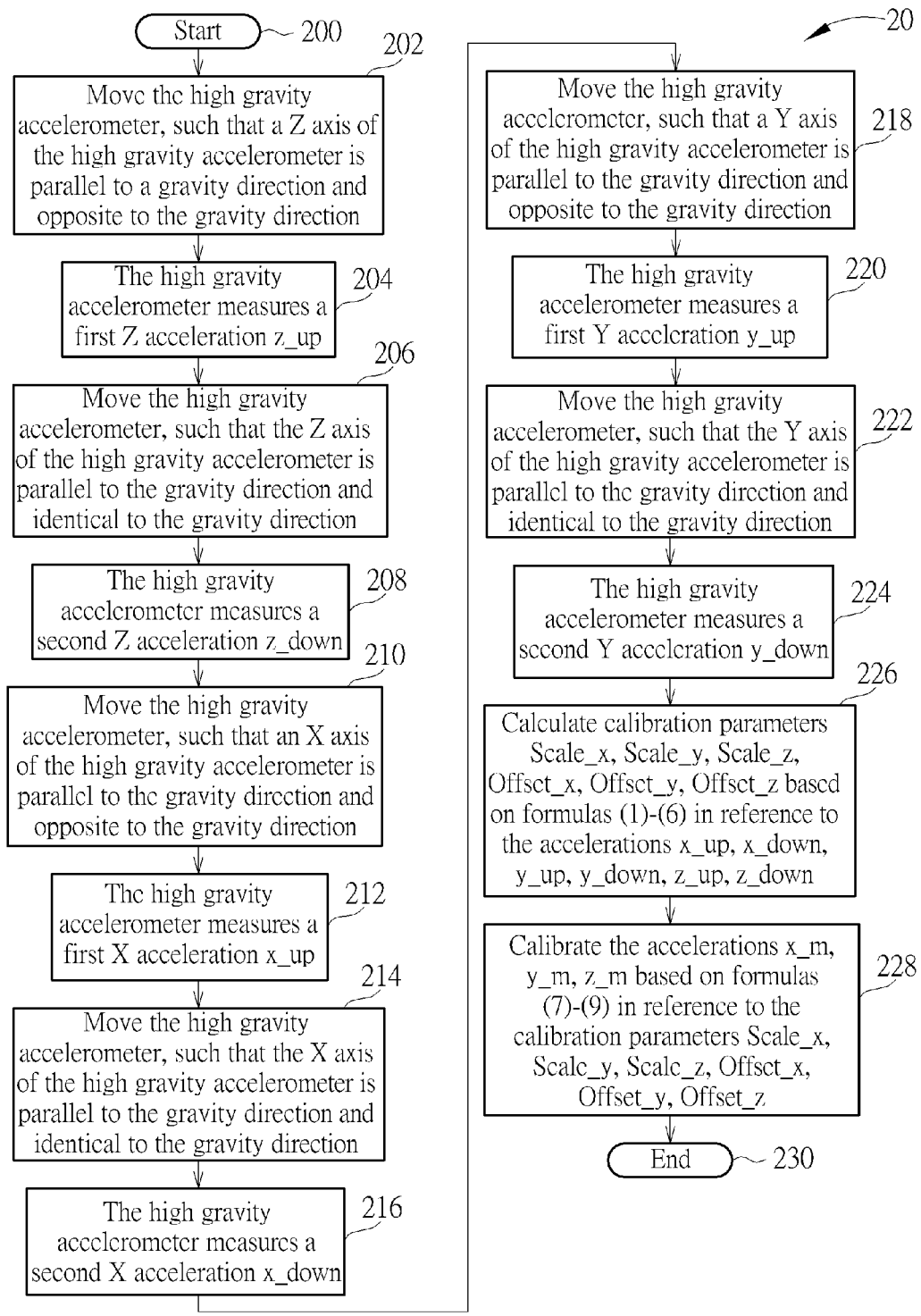
FIG. 2 is a flowchart of a calibration process according to an embodiment of the invention.

Please refer to FIG. 2, which is a flowchart of a calibration process 20 according to an embodiment of the invention. The calibration process 20 is utilized for calibrating a high gravity accelerometer installed in the head 110 of FIG. 1. The calibration process 20 includes the following steps:

Step 200: Start.

Step 202: Move the high gravity accelerometer, such that a Z axis of the high gravity accelerometer is parallel to a gravity direction and opposite to the gravity direction.

Step 204: The high gravity accelerometer measures a first Z acceleration z_up.

Step 206: Move the high gravity accelerometer, such that the Z axis of the high gravity accelerometer is parallel to the gravity direction and identical to the gravity direction.

Step 208: The high gravity accelerometer measures a second Z acceleration z_down.

Step 210: Move the high gravity accelerometer, such that an X axis of the high gravity accelerometer is parallel to the gravity direction and opposite to the gravity direction.

Step 212: The high gravity accelerometer measures a first X acceleration x_up.

Step 214: Move the high gravity accelerometer, such that the X axis of the high gravity accelerometer is parallel to the gravity direction and identical to the gravity direction.

Step 216: The high gravity accelerometer measures a second X acceleration x_down.

Step 218: Move the high gravity accelerometer, such that a Y axis of the high gravity accelerometer is parallel to the gravity direction and opposite to the gravity direction.

Step 220: The high gravity accelerometer measures a first Y acceleration y_up.

Step 222: Move the high gravity accelerometer, such that the Y axis of the high gravity accelerometer is parallel to the gravity direction and identical to the gravity direction.

Step 224: The high gravity accelerometer measures a second Y acceleration y_down.

Step 226: Calculate calibration parameters Scale_x, Scale_y, Scale_z, Offset_x, Offset_y, Offset_z based on formulas (1)-(6) in reference to the accelerations x_up, x_down, y_up, y_down, z_up, z_down.

Step 228: Calibrate the accelerations x_m, y_m, z_m based on formulas (7)-(9) in reference to the calibration parameters Scale_x, Scale_y, Scale_z, Offset_x, Offset_y, Offset_z.

Step 230: End.

$$\text{Scale\_x} = \frac{|x\_up - x\_down|}{G \times 2} \quad \text{formula (1)}$$

$$\text{Scale\_y} = \frac{|y\_up - y\_down|}{G \times 2} \quad \text{formula (2)}$$

$$\text{Scale\_z} = \frac{|z\_up - z\_down|}{G \times 2} \quad \text{formula (3)}$$

$$\text{Offset\_x} = \frac{x\_up + x\_down}{2} \quad \text{formula (4)}$$

$$\text{Offset\_y} = \frac{y\_up + y\_down}{2} \quad \text{formula (5)}$$

$$\text{Offset\_z} = \frac{z\_up + z\_down}{2} \quad \text{formula (6)}$$

$$x\_cali = \frac{x\_m - \text{Offset\_x}}{\text{Scale\_x}} \quad \text{formula (7)}$$

$$y\_cali = \frac{y\_m - \text{Offset\_y}}{\text{Scale\_y}} \quad \text{formula (8)}$$

$$z\_cali = \frac{z\_m - \text{Offset\_z}}{\text{Scale\_z}} \quad \text{formula (9)}$$

In formulas (1)-(9), G represents gravity, i.e. G=9.8 m/s$^2$, and x_cali, y_cali, z_cali respectively represent calibrated X, Y, Z accelerations of the high gravity accelerometer.

According to the calibration process 20, the high gravity accelerometer has to be moved for six times, and the gravity is used as a reference when the X, Y, Z accelerations are measured, to minimize an error of the high gravity accelerometer. That is, a manufacturer can calibrate every high gravity accelerometer based on the calibration process 20 before shipment.

Figure 3:
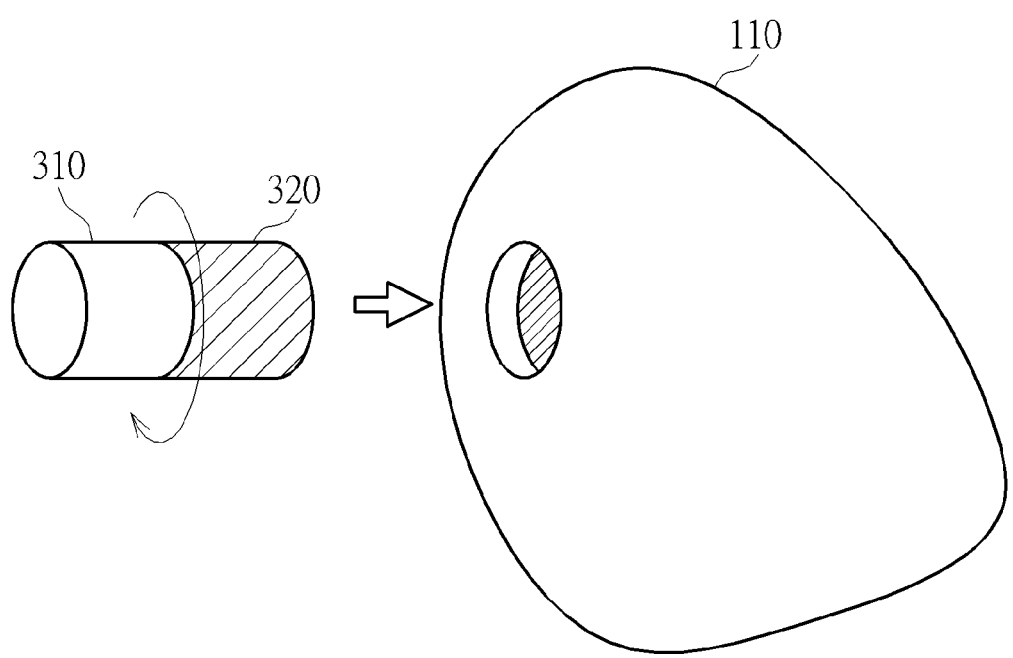
FIG. 3 is a schematic diagram of a head according to an embodiment of the invention.

In a general application, as shown in FIG. 3, a high gravity accelerometer 310 is installed in the head 100. However, a user and the manufacturer may not know a final direction of the high gravity accelerometer 310 in the head 100 when the installation is completed. In such a situation, the moving operations required in Steps 202, 206, 210, 214, 218, 222 are difficult to be performed. In addition, due to limited installation techniques, the manufacturer cannot guarantee that every high gravity accelerometer is installed at the same position in the head 110, which renders Steps 202, 206, 210, 214, 218, 222 more difficult to be performed.

Figure 4:
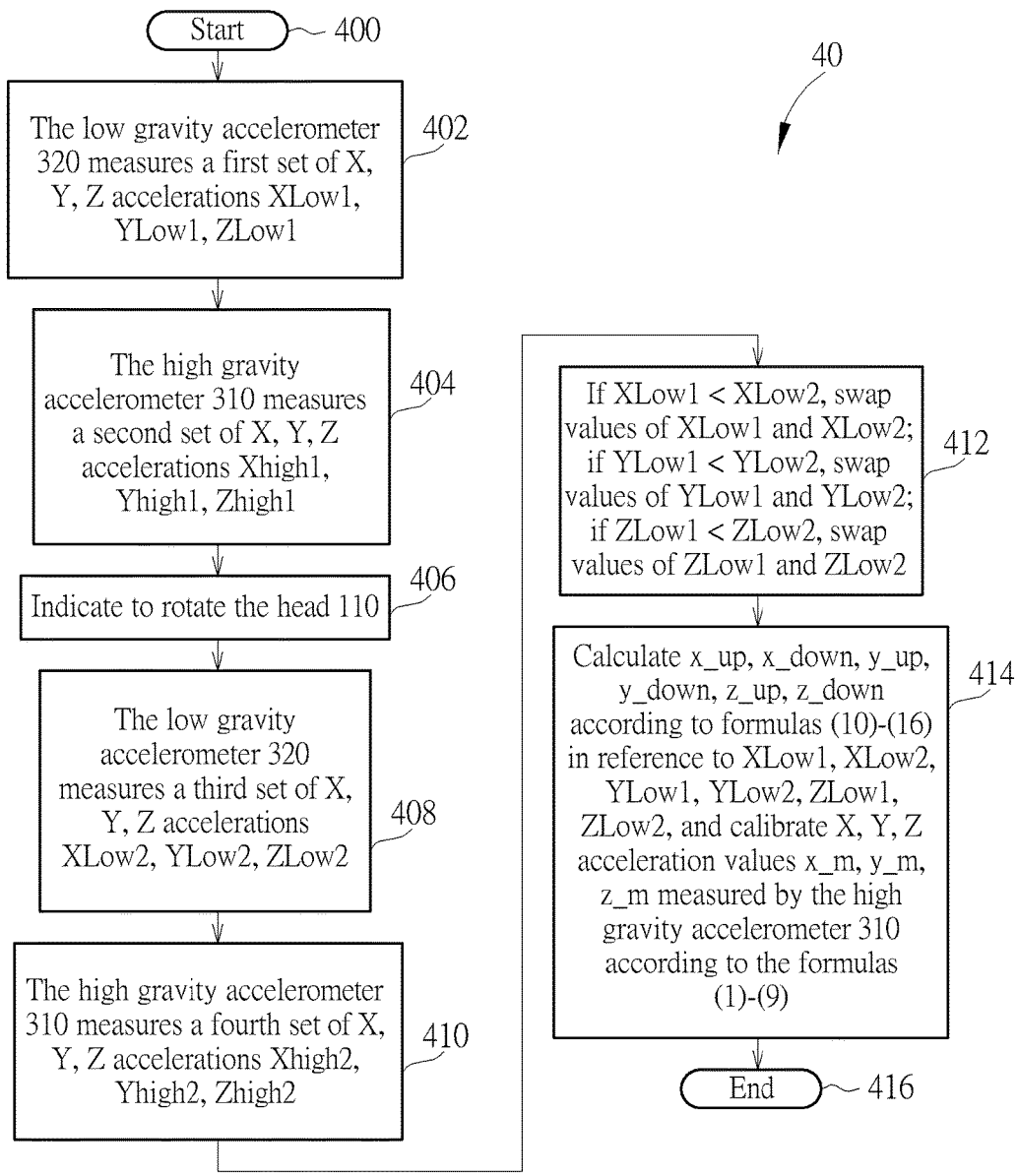
FIG. 4 is a flowchart of a calibration process according to an embodiment of the invention.

For that reason, the invention further provides a calibration process 40 to simplify the calibration process 20. Please refer to FIG. 4, which is a flowchart of the calibration process 40 according to an embodiment of the invention.

The calibration process 40 is also utilized for calibrating the high gravity accelerometer 310 of the head 110. Also, as shown in FIG. 3, a low gravity accelerometer 320 is installed together with the high gravity accelerometer 310 in the head 110. The calibration process 20 includes the following steps:

Step 400: Start.

Step 402: The low gravity accelerometer 320 measures a first set of X, Y, Z accelerations XLow1, YLow1, ZLow1.

Step 404: The high gravity accelerometer 310 measures a second set of X, Y, Z accelerations Xhigh1, Yhigh1, Zhigh1.

Step 406: Indicate to rotate the head 110.

Step 408: The low gravity accelerometer 320 measures a third set of X, Y, Z accelerations XLow2, YLow2, ZLow2.

Step 410: The high gravity accelerometer 310 measures a fourth set of X, Y, Z accelerations Xhigh2, Yhigh2, Zhigh2.

Step 412: If XLow1<XLow2, swap values of XLow1 and XLow2; if YLow1<YLow2, swap values of YLow1 and YLow2; if ZLow1<ZLow2, swap values of ZLow1 and ZLow2.

Step 414: Calculate x_up, x_down, y_up, y_down, z_up, z_down according to formulas (10)-(16) in reference to XLow1, XLow2, YLow1, YLow2, ZLow1, ZLow2, and calibrate X, Y, Z acceleration values x_m, y_m, z_m measured by the high gravity accelerometer 310 according to the formulas (1)-(9).

Step 416: End.

$$\text{Scale\_Rate} = \frac{XHigh1 - XHigh2}{XLow1 - XLow2} \quad \text{formula (10)}$$

$$x\_up = XHigh1 + (1 - XLow1) \times \text{Scale\_Rate} \quad \text{formula (11)}$$

$$x\_down = XHigh2 + (1 - XLow2) \times \text{Scale\_Rate} \quad \text{formula (12)}$$

$$y\_up = YHigh1 + (1 - YLow1) \times \text{Scale\_Rate} \quad \text{formula (13)}$$

$$y\_down = YHigh2 + (1 - YLow2) \times \text{Scale\_Rate} \quad \text{formula (14)}$$

$$z\_up = ZHigh1 + (1 - ZLow1) \times \text{Scale\_Rate} \quad \text{formula (15)}$$

$$z\_down = ZHigh2 + (1 - ZLow2) \times \text{Scale\_Rate} \quad \text{formula (16)}$$

In short, the calibration process 40 no longer requires to move the high gravity accelerometer 310 for six times, but still can calculate the accelerations x_up, x_down, y_up, y_down, z_up, z_down of the calibration process 20. Next, according to the formulas (1)-(9), the calibrated accelerations x_cali, y_cali, z_cali can be calculated. As a result, the high gravity accelerometer 310 merely has to be moved for once since an initial position of the head 110 can be a random position. Moreover, axes of the high gravity accelerometer 310 are no longer required to be aligned with the gravity direction, and a user or manufacturer no longer has to know an installation position of the high gravity accelerometer 310. These advantages can simplify calibration processes of the golf club 100. For example, when the golf club 100 is sold to a consumer, a standard calibration process should not include a step of taking out the high gravity accelerometer 310 from the head 110 since the consumer may not has the skills to reinstall the head 110, and the high gravity accelerometers 310 may be initially installed at different positions of the golf clubs 100. Therefore, the calibration processes should not relate to the installation position to prevent errors. Since the calibration process 40 merely has to move the head 110 once, and does not relate to the installation position of the high gravity accelerometer 310, the calibration process 40 meets those requirements.

On the other hand, the formulas (10)-(16) make use of advantages that the low gravity accelerometer 320 has a smaller error than the high gravity accelerometer 310 and is installed together with the high gravity accelerometer 310 (measure the same acceleration). Accordingly, in reference to the accelerations XLow1, XLow2, YLow1, YLow2, ZLow1, ZLow2 measured by the low gravity accelerometer 320, the accelerations x_up, x_down, y_up, y_down, z_up, z_down of the high gravity accelerometer 320 can be estimated. As a result, the user or the manufacturer no longer has to align the axes of the high gravity accelerometers 310 for six times, which can significantly enhance calibration efficiency and convenience.

Figure 5:
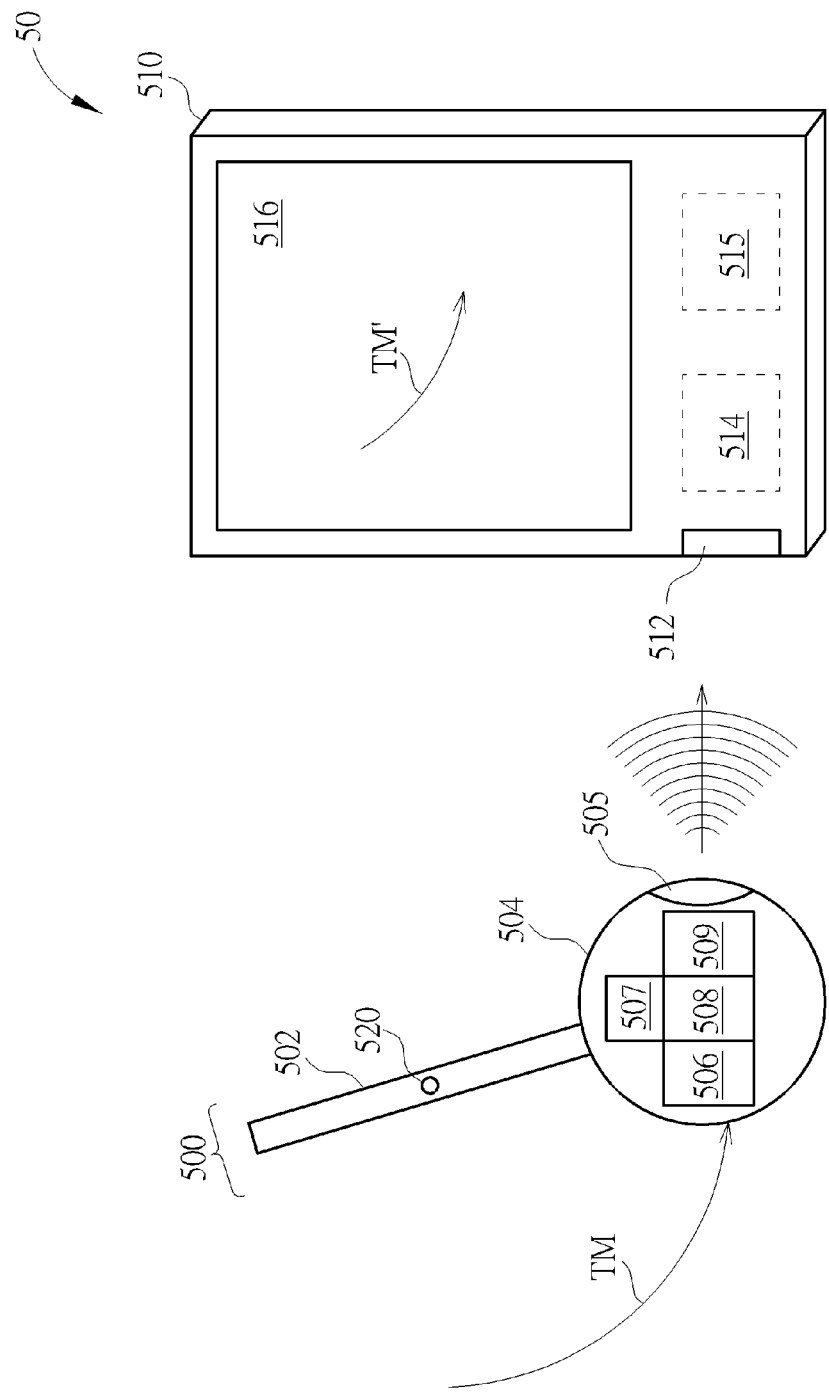
FIG. 5 is a schematic diagram of a calibration system according to an embodiment of the invention.

Also, the calibration process 40 can be performed by an electronic device for automation. Please refer to FIG. 5, which is a calibration system 50 according to an embodiment of the invention. The calibration system 50 includes a sports equipment 500 and an electronic device 510. The sports equipment 500 includes a shaft 502, a head 504 and an indicative button 520. The head 504 is installed at one end of the shaft 502, and includes a high gravity accelerometer 506, a low gravity accelerometer 508, a processing means 507, a storage unit 509 and an interface unit 505. The high gravity accelerometer 506 is identical to the high gravity accelerometer 310, and the low gravity accelerometer 508 is identical to the low gravity accelerometer 320. Details of the high and low gravity accelerometers 506, 508 are discussed in the above, and are not further narrated herein again. The storage unit 509 is utilized for storing a program code, which is utilized for instruct the processing means 507 to perform Steps 402-410. The indicative button 520 is a press button for the user to activate the calibration process 40, and is further utilized for indicating timing to rotate the head 110. For example, when Steps 402, 404 are finished, the processing means 507 may drive and light the indicative button 520, such that the user can rotate the head 110 accordingly. The interface unit 505, such as a Bluetooth or Wi-Fi module, is utilized for outputting data to the electronic device 510. The electronic device 510, such a smartphone or a personal computer, includes a receiving unit 512, a processing means 514, a storage unit 515 and a display unit 516. The receiving unit 512 is utilized for receiving the data transmitted by the interface unit 505. The storage unit 515 is utilized for storing a program code, which is utilized for instructing the processing means 514 to perform Steps 412, 414 to calculate the calibrated acceleration values x_cali, y_cali, z_cali, and simulating a motion trace TM of the head 504 according to the calibrated acceleration values x_cali, y_cali, z_cali. Finally, a simulated motion trace TM' is displayed on the display unit 516. As a result, the user can repeatedly examine the simulated motion trace TM' to improve athletic skills.

Note that, Steps 412, 414 of the calibration process 40 may be performed by the processing means 507 of the sports equipment 500 or the processing means 514 of the electronic device 510. That is, the interface unit 505 may output raw data, such as the accelerations XLow1, XLow2, YLow1, YLow2, ZLow1, ZLow2, XHigh1, XHigh2, YHigh1, YHigh2, ZHigh1, ZHigh2, or calculated data, such as the calibrated acceleration values x_cali, y_cali, z_cali, to the electronic device 510.

Execution details of the calibration process 40 performed by the calibration system 50 can be understood in reference to the above discussion, and are not further narrated herein again.

To sum up, in order to minimize the error of the high gravity accelerometer, the invention teaches to estimate the calibration parameters of the high gravity accelerometer based on the accelerations measured by the low gravity accelerometer, so as to simplify the calibration process and enhance convenience. As a result, the user or the manufacturer can employ the automatic calibration process to quickly calibrate the high gravity accelerometer of the sports equipment.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A sports equipment, comprising:
   a shaft;
   a head, installed at one end of the shaft, comprising:
   a first accelerometer;
   a second accelerometer;
   a processing means;
   a storage unit, for storing a program code, wherein the program code is utilized for instructing the processing means to perform a calibration process; and
   an interface unit, for outputting data; and
   an indicative button, for activating the calibration process, wherein the calibration process only involves measurements of four sets of X, Y, Z accelerations in a Cartesian coordinate system, and comprises:
   instructing the second accelerometer to measure a first set of X, Y, Z accelerations in the Cartesian coordinate system;
   instructing the first accelerometer to measure a second set of X, Y, Z accelerations in the Cartesian coordinate system;
   driving the indicative button to display a signal, wherein the signal is utilized for indicating to rotate the head;
   instructing the second accelerometer to measure a third set of X, Y, Z accelerations in the Cartesian coordinate system;
   instructing the first accelerometer to measure a fourth set of X, Y, Z accelerations in the Cartesian coordinate system;
   calibrating X, Y, Z acceleration values measured by the first accelerometer according to the first, second, third and fourth sets of X, Y, Z accelerations; and
   instructing the interface unit to output the calibrated X, Y, Z acceleration values;
   wherein the first accelerometer is a high gravity accelerometer, and the second accelerometer is a low gravity accelerometer.

2. The sports equipment of claim 1, wherein the calibration process further comprises:
   instructing the interface unit to output the first, second, third and fourth sets of X, Y, Z accelerations.

3. The sports equipment of claim 1, wherein:
   the first set comprises a first X acceleration XLow1, a first Y acceleration YLow1 and a first Z acceleration ZLow1;
   the second set comprises a second X acceleration XHigh1, a second Y acceleration YHigh1 and a second Z acceleration ZHigh1;
   the third set comprises a third X acceleration XLow2, a third Y acceleration YLow2 and a third Z acceleration ZLow2; and the fourth set comprises a fourth X acceleration XHigh2, a fourth Y acceleration YHigh2 and a fourth Z acceleration ZHigh2.

\* \* \* \* \*